United States Patent [19]
Ikeda et al.

[11] Patent Number: 5,464,380
[45] Date of Patent: Nov. 7, 1995

[54] SHOE SOLE FOR LEG APPARATUS

[75] Inventors: Kiichi Ikeda, Tsuchiura; Shuji Kajita; Tetsu Iwatsuki, both of Tsukuba, all of Japan

[73] Assignees: Agency of Industrial Science & Technology; Ministry of International Trade & Industry, both of Tokyo, Japan

[21] Appl. No.: 219,305

[22] Filed: Mar. 28, 1994

[30] Foreign Application Priority Data

Mar. 31, 1993 [JP] Japan .................... 5-097309

[51] Int. Cl.⁶ .................... A61F 5/00; A43B 5/00
[52] U.S. Cl. .................... 601/29; 482/77; 36/81; 601/27; 601/100; 602/23
[58] Field of Search .................... 602/5, 10, 23, 602/27–29; 36/97, 81; 601/27, 29, 31, 100; 482/75–77; 128/882

[56] References Cited

U.S. PATENT DOCUMENTS

| | | | |
|---|---|---|---|
| 1,613,538 | 1/1927 | Schad | 482/77 X |
| 2,021,801 | 11/1935 | Meyer | 601/27 X |
| 2,345,085 | 3/1944 | Albert et al. | 482/77 X |
| 4,523,395 | 6/1985 | Borsoi | 36/81 X |
| 4,912,859 | 4/1990 | Ritts | 482/77 X |

FOREIGN PATENT DOCUMENTS

| | | | |
|---|---|---|---|
| 25330 | 7/1907 | Brazil | 36/81 |
| 494373 | 9/1919 | France | 36/81 |
| 4352961 | 12/1992 | Japan . | |

*Primary Examiner*—Linda C. M. Dvorak
*Attorney, Agent, or Firm*—Oblon, Spivak, McClelland, Maier & Neustadt

[57] ABSTRACT

A leg apparatus shoe sole has an upper sole member and a lower sole member interconnected by expanders so as to be movable towards and away from each other wherein the expanders are connected with a remote actuator by a drive wire. The actuator is operated to reduce the thickness of the shoe sole when the associated leg is the free leg and to increase its thickness when the associated leg is the supporting leg.

7 Claims, 5 Drawing Sheets

5,464,380

SHOE SOLE FOR LEG APPARATUS

BACKGROUND OF THE INVENTION

1. Field of the Invention

This invention relates to a shoe sole for a leg apparatus that serves as an ambulatory apparatus for persons paralyzed in both legs.

2. Description of the Prior Art

Injuries to the cervical or spinal vertebrae caused by automobile accidents, falls and the like can paralyze the upper and lower limbs. Many persons handicapped by such injuries are instantaneously committed to life in a wheel chair. Although wheelchairs provide the handicapped with good mobility, they have numerous drawbacks from medical and psychological viewpoints. Among the ambulatory apparatuses devised for overcoming these disadvantages of the wheelchair is the parawalker developed in the U.K. The user of,this apparatus has all of his or her lower body aside from the hip joints immobilized and moves forward by twisting the upper body. Since ambulation by twisting requires clearance between the free leg and the floor, the user has to tilt his or her body by a large angle. Walking therefore becomes a very strenuous activity. It is possible to eliminate the need for large body tilting and reduce the burden on the user by shortening the length of the free leg from the time it leaves the floor and lengthening it again when it comes in contact with the floor to once more serve as the supporting leg. As a mechanism for achieving alternate lengthening and shortening of the legs there has been developed a leg apparatus able to vary the thickness of a shoe sole. (See Japanese Patent Public Disclosure Hei 4(1992)-352961, for example.)

FIG. 7 shows such a sole developed earlier for enabling thickness adjustment. As illustrated, the sole 100 has a two-tier sole structure consisting of an upper sole member 101 and a lower sole member 102 connected by a pair of linkages 106 each constituted of a pair of links 103 and 104 and a pivot 105. The thickness of the sole 100 can be changed by bending land straightening the linkages 106 to move the upper sole member 101 and the lower sole member 102 toward and away from each other. As indicated by reference numerals 107 in FIG. 7, pneumatic cylinders or the like can be used as the actuators for bending and straightening the linkages 106. Since the actuators 107 are mounted between the upper and lower sole members 101, 102 of the sole 100, however, they increase the weight of the sole 100 and place a greater burden on the user. In addition, the presence of the actuators 107 between the upper and lower sole members 101, 102 limits the degree to which the thickness of the sole 100 can be reduced.

The present invention was accomplished in view of the foregoing circumstances and has as its object to provide a leg apparatus shoe sole which enables the thickness of the sole to be changed with ease, does not place a heavy load on the feet of the user, is simple in structure and allows great reduction of the thickness of the shoe sole on the free foot.

SUMMARY OF THE INVENTION

For achieving the aforesaid object, the present invention provides a leg apparatus shoe sole with a two-tier structure having vertically spaced upper and lower sole members movable toward and away from each other, the shoe sole comprising: expanders for expandably connecting the upper and lower sole members and drive means for driving the expanders, the expanders including at least a pair of linkages each constituted of an upper link and a lower link swingably joined by a first pivot, the upper end of the upper link being connected with the upper sole by a second pivot, and the lower end of the lower link being connected with the lower sole by a third link, and the drive means including at least one actuator located at a position remote from the linkages, at least one drive wire means driven by the actuator for synchronously driving the pair of linkages between a basic attitude in which the linkages are bent outward and an expanded attitude in which the linkages are straightened vertically, and restoring means for restoring the expanded linkages to their basic attitude.

Various other objects, features and attendant advantages of the present invention will be more fully appreciated as the same becomes better understood from the following detailed description when considered in connection with the accompanying drawings in which like reference characters designate like or corresponding parts throughout the several views and wherein:

BRIEF DESCRIPTION OF THE DRAWINGS

FIG. 4(*b*) is a plan view of the upper sole member of a shoe sole according to this invention.

FIG. 4(*c*) is a plan view of the lower sole member of a shoe sole according to this invention.

DESCRIPTION OF THE PREFERRED EMBODIMENT

Figure 1:
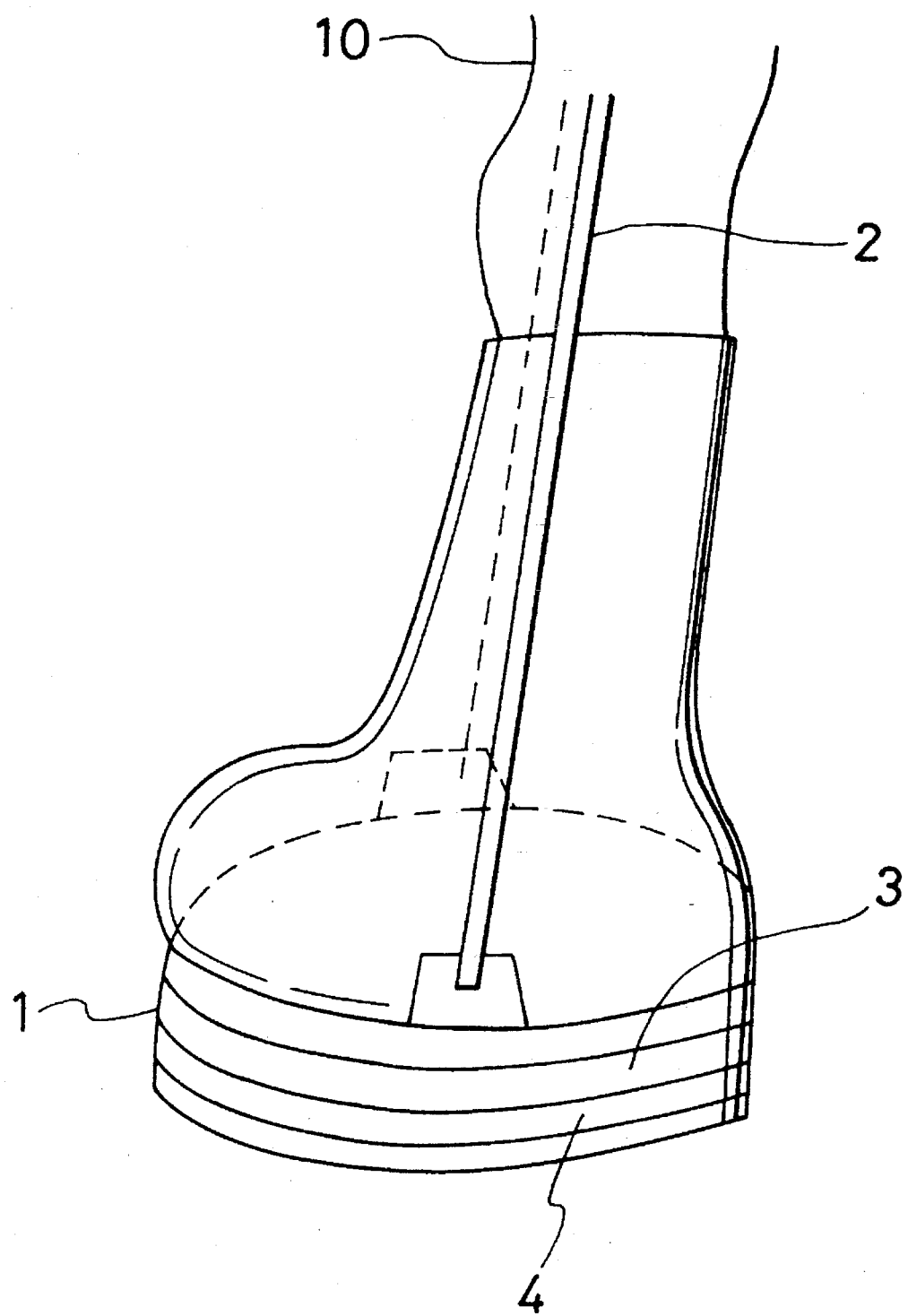
FIG. 1 is a schematic view of a leg apparatus including a shoe sole according to,this invention.

An embodiment of the leg apparatus shoe sole according to this invention will now be explained in detail with reference to the drawings. The shoe sole, designated by reference numeral 1 in FIGS. 1 to 3, constitutes the lower end of a leg apparatus 2 to be worn by a person (the user) who is paralyzed from the waist down. The shoe sole 1 has a two-tier structure comprising an upper sole member 3 and a lower sole member 4 spaced from each other vertically. As shown in FIGS. 4(*b*) and 4(*c*), the upper sole member 3 and the lower sole member 4 are rectangular in plan view. The upper surface of the upper sole member 3 is made of, for example, a metal such as aluminum and the bottom surface of the lower sole member 4, which makes contact with the ground, is made of rubber, synthetic resin or the like.

The four corners of the upper sole member 3 are formed with rectangular notches 51 and an upright connecting arm 52 is fastened in each notch.

Figure 2:
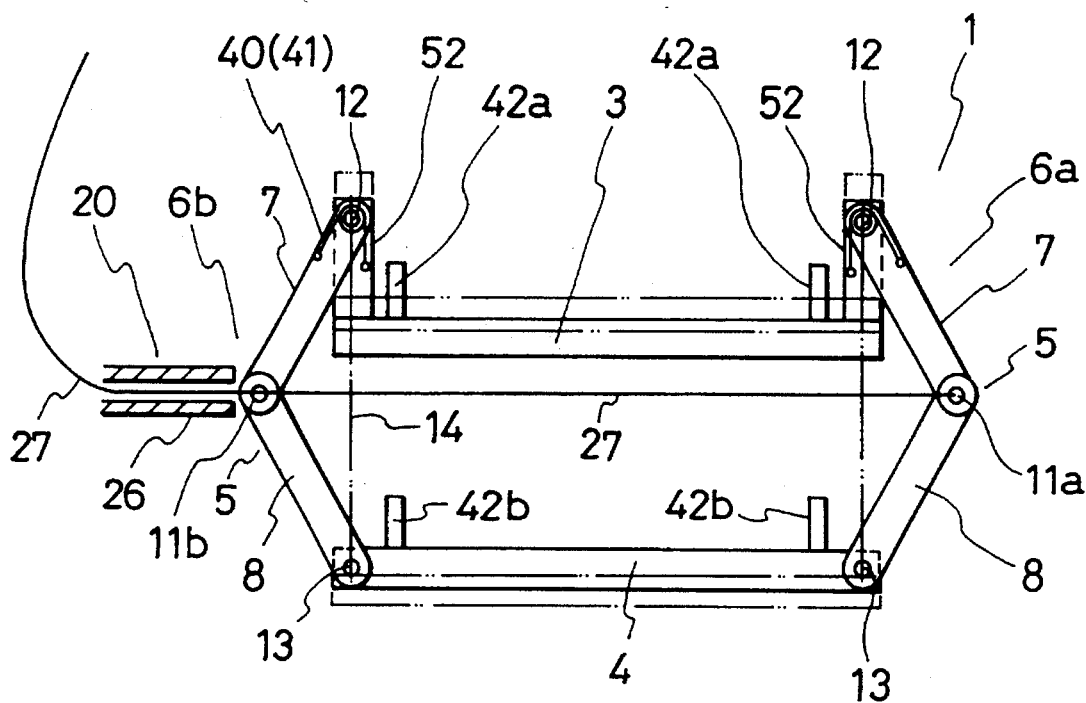
FIG. 2 is a sectional view of a shoe sole according to this invention showing the sole at near maximum thickness.
Figure 3:
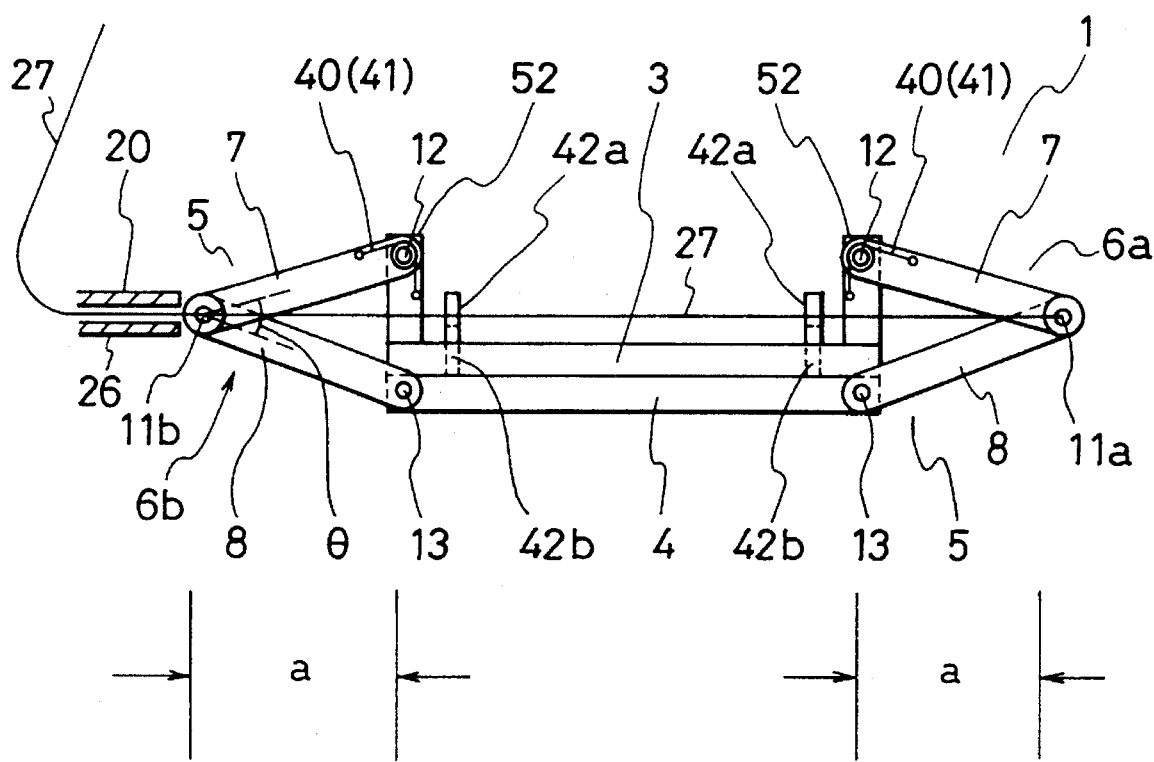
FIG. 3 is a sectional view of a shoe sole according to this invention showing the sole at near minimum thickness.
Figure 4:
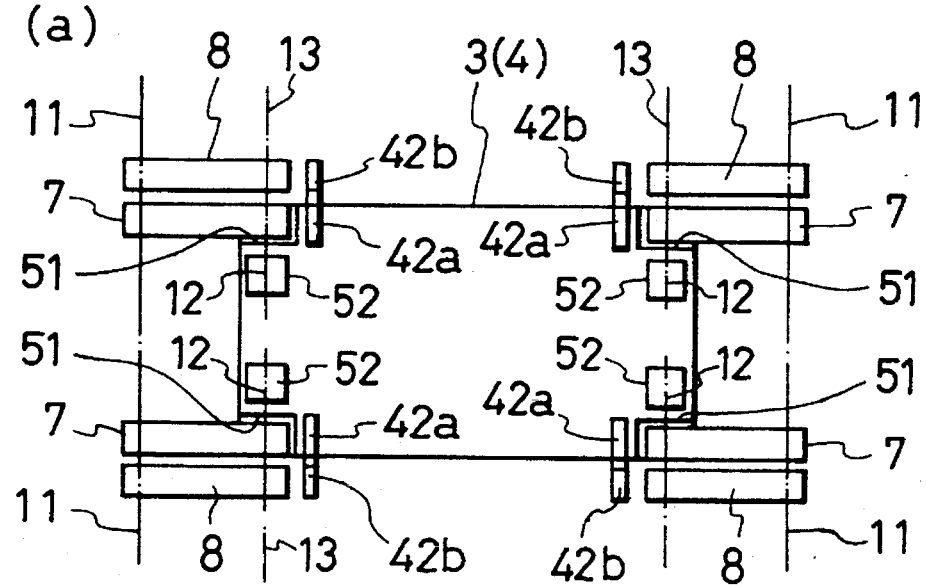
FIG. 4(*a*) is a plan view of a shoe sole according to this invention.
Figure 4:
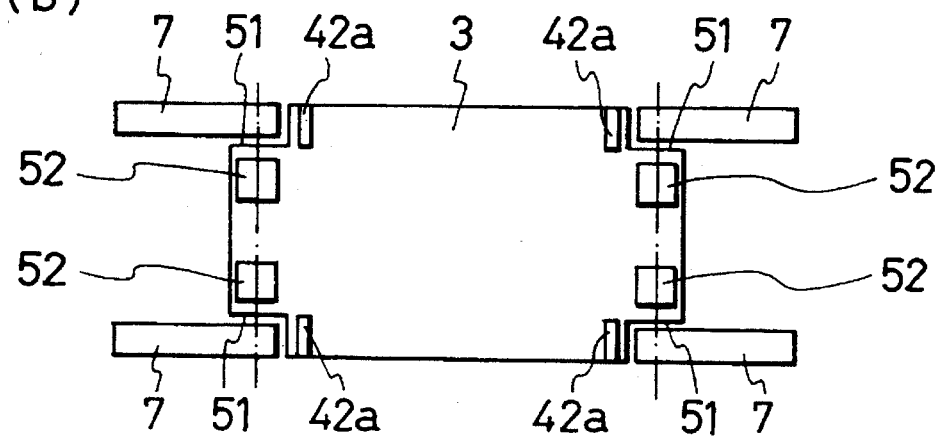
Figure 4:
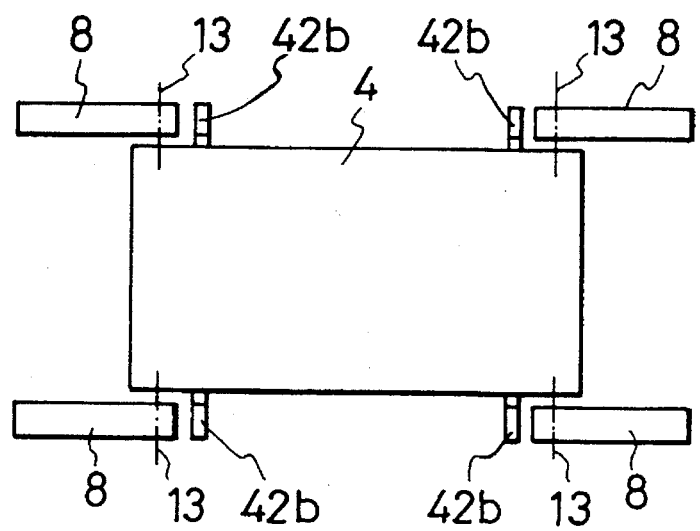

As shown in FIGS. 2 and 3, the upper sole member 3 and the lower sole member 4 are connected at opposite ends by pairs of expanders 5 so as to be vertically movable toward and away from each other. When the separation between the upper and lower sole members 3 and 4 is large, the thickness of the sole is large, and when it is small, the thickness of the sole is small. The expanders 5 comprise a pair of first linkages 6a connecting the forward ends of the upper and lower sole members 3 and 4 and a pair of second linkages 6b connecting the rearward ends of the upper and lower sole members 3. Each of the first and second linkages 6a, 6b comprises an upper link 7 and a lower link 8 and a first pivot 11a or 11b swingably connecting the lower end of the upper link 7 with the upper end of lower link 8.

The upper end of each upper link 7 is swingably connected to near the upper end of one of the connecting arms 52 standing upright on the upper sole member 3 by a second pivot shaft 12, while the lower end of each lower link 8 is swingably connected to the lower sole member 4 by a third pivot shaft 13. The linkages 6a and 6b are in their most expanded state when the upper and lower links 7 and 8 lie along a vertical line. When the linkages 6a, 6b are in this expanded attitude, the vertical distance between the upper and lower sole members 3 and 4 is greatest, which is to say that the thickness of the shoe sole 1 is maximum (see broken lines in FIG. 2)

A stop 42b is provided to extend upward from the side edge of the lower sole member 4 at a position just inward of the point of connection of each lower link 8 (four stops in total). In addition, a stop 42a is provided to extend upward from the upper surface of the upper sole member 3 at a position just inward of the point of connection of each upper link 7 (four stops in total). The stops 42a, 42b prevent the linkages 6a, 6b from bending farther inward than the expanded attitude 14 indicated in FIG. 2.

The height of the connecting arms 52 which swingably support the upper links 7 is selected such that the angle θ between the upper link 7 and the lower link 8 (see FIG. 3) will be greater than zero when the shoe sole 1 is thinnest and the upper and lower sole members 3 and 4 are almost in contact with each other. This is to reduce the amount of force required to expand the sole from its thinnest state.

Figure 5:
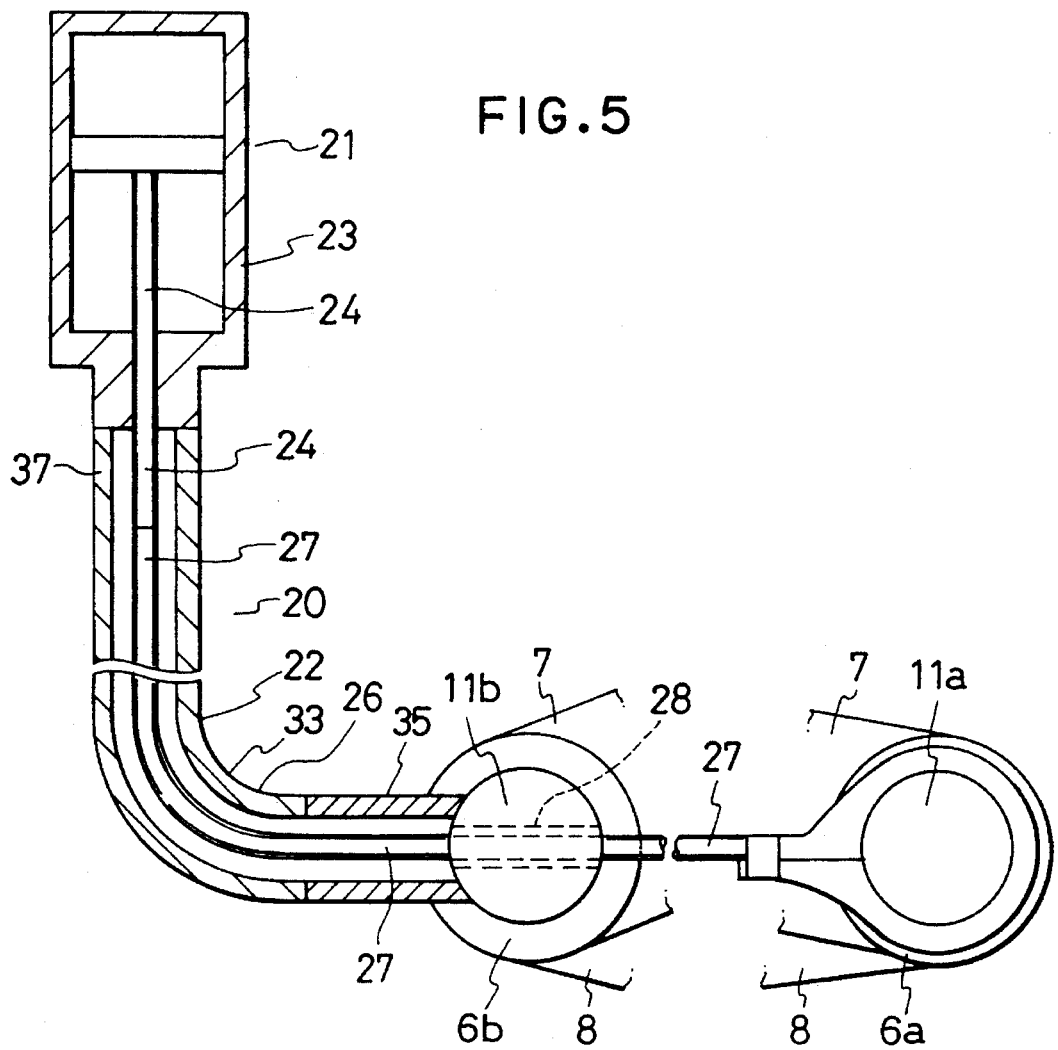
FIG. 5 is a sectional view of the drive mechanism of a shoe sole according to this invention.
Figure 6:
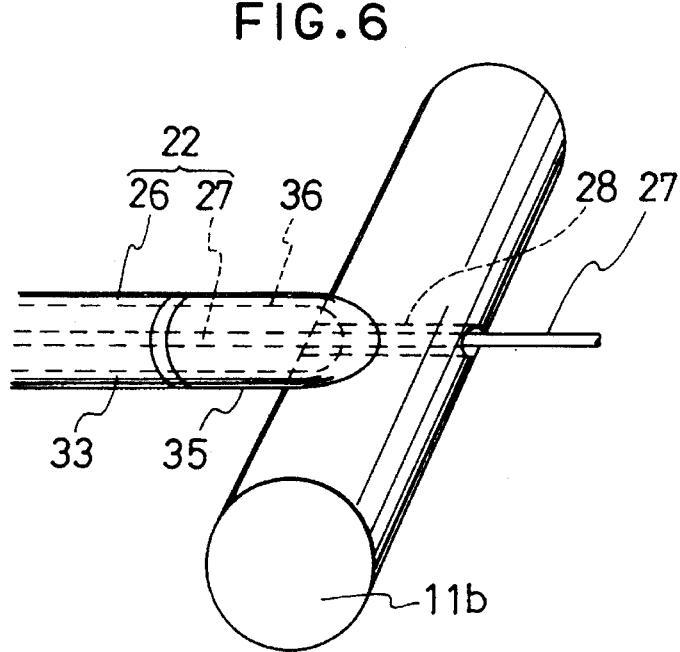
FIG. 6 is a perspective view showing how the drive mechanism of FIG. 5 is attached to a pivot of the shoe.
Figure 7:
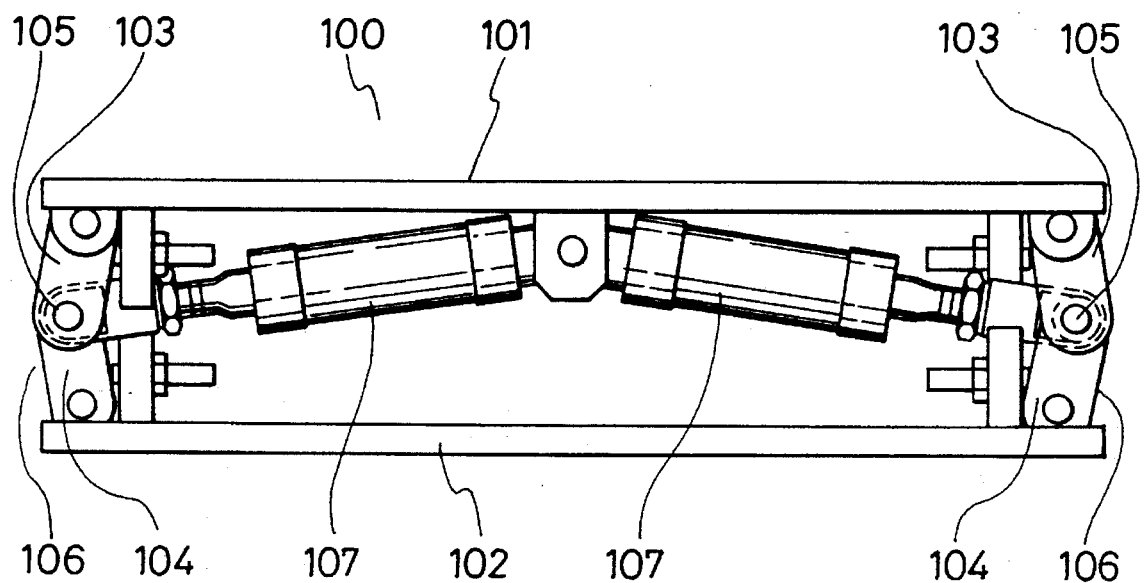
FIG. 7 is a sectional view of a prior art leg apparatus shoe sole.

The linkages 6a, 6b of the expanders 5 on each side of the shoe sole 1 are bent and straightened by a drive mechanism 20. As shown in FIGS. 5 and 6, each drive mechanism 20 is equipped with an actuator 21 and a drive wire 22. The actuator 21 comprises a stationary member 23 and a moving member 24. It can be constituted as a pneumatic cylinder, for example. The actuator 21 is attached to the leg apparatus 2 in the vicinity of the waist of the user. The drive wire 22 consists of a tubular outer cable 26 and an inner wire 27 that passes through the interior of the outer cable 26 so as to be movable in the longitudinal direction with respect to it. In other words, the inner wire 27 is enclosed by the outer cable 26 but is free to move longitudinally inside the outer cable 26. The lower end of the inner wire 27 is connected to the point of connection between the upper and lower links 7 of the linkage 6a. Although the end of the inner wire 27 is connected to the first pivot 11a in the illustrated embodiment, it can instead be connected to near the lower end of the upper link 7 or near the upper end of the lower link 8. In the illustrated embodiment, the inner wire 27 passes back through the first pivot 11b of the second linkage 6b and the outer cable 26 to have its base end connected to the moving member 24 of the actuator 21. The inner wire 27 does not have to pass through the second linkage 6b at the first pivot 11b, however, and can instead pass through it in the vicinity of the lower end of the upper link 7 or in the vicinity of the upper end of the lower link 8. In any case, preferably it passes at a point corresponding to the place where, as explained later, the tip of the outer cable 26 abuts linkage 6b as shown in FIG. 5. In the illustrated embodiment, the inner wire 27 passes through a through-hole 28 formed to pass diametrically through the first pivot 11b. The leading end 33 of the outer cable 26 is fastened to the first pivot 11b of the second linkage 6b by a fastener 35. The fastener 35 is formed with a through-hole 36 which is aligned with the through-hole 28 of the first pivot 11b and the inner wire 27 passes through the aligned holes. The base end 37 of the outer cable 26 is fixed to the stationary member 23 of the actuator 21.

A shape restoring mechanism 40 is provided between each upper link 7 and the upper sole member 3. In the illustrated embodiment, each of the shape restoring mechanisms 40 is constituted by a spring 41 having one end fixed to the associated connecting arm 52 and the other end fixed to the upper link 7 so as to urge the upper link 7 upward and thus urge the linkage 6a or 6b to bend outward. The invention is not limited to this arrangement, however, and any spring means providing a similar action can be used instead.

As shown in FIG. 3, when the drive mechanism 20 is not acting on the linkages 6a and 6b, the springs 41 urge the upper and lower sole members 3, 4 almost into contact with each other (the basic attitude), as is possible since the stops 42a, 42b do not interfere with each other or with the upper and lower sole members 3, 4.

The operation of the shoe sole of the foregoing configuration will now be explained.

When a leg of the user 10 becomes the free leg, i.e., when it begins to move forward after completing a rearward kick, it is necessary to reduce the thickness of the shoe sole 1. This is achieved not by the actuators 21 but by the action of the springs 41 pushing the upper links 7 outward when the linkages 6a, 6b are free of the action of the actuators 21, with the result that the linkages 6a , 6b are bent outward so that the upper and lower sole members 3, 4 approach each other and enable the shoe sole 1 to assume minimum thickness. Then when the same leg of the user 10 becomes the supporting leg, i.e., when it begins a rearward kick after reaching the limit of its forward swing, it is necessary to increase the thickness of the shoe sole 1. For this, the actuators 21 are operated to pull the inner wires 27. As will be understood from FIG. 3, the force of each inner wire 27 acts to pull in the first pivot 11a of the associated linkage 6a inward by a distance , thus causing the linkage 6a to straighten, while the reactive force of the outer cable 26 acts to push in the first pivot 11b by the same distance , thus causing the second linkage 6b to straighten. As a result, the shoe sole 1 expands to a prescribed thickness. When the force of the actuator 21 is released, the leaf or coil springs 41 attached to the upper portions of the respective upper links 7 apply a moment of force to the linkages 6a, 6b so as to bend them outward, whereby the shoe sole 1 is made thin again. When the thickness of the shoe sole 1 is minimum, the upper and lower sole members 3, 4 are almost in contact with each other. The movement of the upper sole members 3, 4 toward each other is not hindered since the upper links 7 and the stops 42a, 42b are located so as not to interfere with each other or with the upper and lower sole members 3, 4. Since the height of the connecting arms 52 is determined such that an angle θ (θ>0) is maintained between the upper links 7 and the lower links 8 when the distance between the upper sole members 3, 4 is minimum, the linkages are not allowed to move to their dead points and can be readily expanded again in the next walking phase.

When a load is applied from above to the linkages 6a, 6b at the time they are in their expanded attitude 14, they are subject to a force acting to bend them inward or outward. This is not a problem, however, since outward bending of the linkages 6a, 6b is prevented by the pulling force of the inner wire 27 and the pushing force of the outer cable 26, while inward bending thereof is prevented by their collision with the stops 42a, 42b. As a result, the expanded state of the shoe sole 1 can be maintained.

Since the shoe sole 1 configured in the manner described in the foregoing does not require the actuators 21 to be located between the upper and lower sole members 3, 4 but only the inner wires 27 and the stops 42a, 42b to be located therebetween, the weight of the shoe sole is not substantially increased. In addition, the fact that the actuators 21 are not present inside the shoe sole means that they do not hinder the folding of the linkages 6a, 6b when the thickness of the shoe sole 1 is reduced. The degree to which the thickness of the shoe sole can be reduced is thus proportionally greater and, as a result, the range over which its thickness can be varied is also proportionally greater. Since these features of the shoe sole make it possible to avoid increasing the burden on the user, the user is able to walk with greater ease. In addition, the elimination of linkage dead points ensures smooth linkage bending and straightening.

In the shoe sole 1 constituted as described in the foregoing, the sole thickness can easily be varied over a range of 30–40 mm by operation of the actuators and linkages. Further, since the actuators are located at a position remote from the linkages and not between the upper and lower soles, a heavy load does not act on the user's feet. The invention thus provides a shoe sole for a leg apparatus that is simple in structure and allows great reduction of the thickness of the shoe sole on the free foot.

What is claimed is:

1. A leg apparatus, comprising:

a shoe having an upper sole member and a lower sole member disposed under said upper sole member;

expanders connected to said upper and lower sole member, said expanders vertically moving the upper and lower sole members toward and away from each other and including at least one pair of forward and rearward linkages, each of said linkages having an upper link and lower link swingably joined by a first pivot, with the upper link being connected at an upper end to said upper sole member by a second pivot and the lower link being connected at a lower end to said lower sole member by a third pivot; and a drive mechanism driving said expanders and including at least one actuator located at a position remote from said upper and lower sole members and outside of the shoe, at least one drive wire driven by the actuator and synchronously driving the pair of linkages between a basic attitude in which the linkages are bent outward and an expanded attitude in which the linkages are straightened vertically; and a restoring mechanism restoring the expanded linkages to their basic attitude.

2. A shoe sole according to claim 1, wherein a stop is provided inward of position where the upper link is connected with the upper sole and inward of a position where the lower link is connected with the lower sole.

3. A shoe sole according to claim 1, wherein the upper and lower links are connected to the upper and lower soles such that an angle formed between each upper link and the lower link is greater than zero when the distance between the upper and lower soles in at a minimum.

4. A shoe sole according to claim 1, wherein the drive mechanism comprises a tubular outer cable and an inner wire passing therethrough, the outer cable being connected with the rearward linkage of the pair of linkages and the inner wire being connected with the forward linkage of the pair of linkages.

5. A shoe sole for a leg apparatus, the shoe sole comprising:

an upper and lower sole member;

expanders expandably connecting the upper and lower sole members;

a drive mechanism driving the expanders;

the expanders including at least one pair of linkages, each of the linkages having an upper link and a lower link, a first pivot swingably adjoining the upper and lower link, a second pivot connecting an upper end of the upper link with the upper sole, and a third pivot connecting a lower end of the lower link with the lower sole;

a drive mechanism including at least one actuator located at a position remote from the upper and lower link, at least one drive wire driven by the actuator, said drive wire synchronously driving the pair of linkages between a basic attitude in which the linkages are bent outward and an expanded attitude in which the linkages are straightened vertically, and a restoring mechanism restoring the expanded linkages to their basic attitude wherein the drive mechanism comprises a tubular outer cable and an inner wire passing therethrough, the outer cable being connected with the rearward linkage of the pair of linkages and the inner wire being connected with the forward linkage of the pair of linkages.

6. A shoe sole according to claim 5, wherein a stop is provided inward of a position where the upper link is connected with the upper sole and inward of a position where the lower link is connected with the lower sole.

7. A shoe sole according to claim 5, wherein the upper and lower links are connected to the upper and lower soles such that an angle formed between each upper link and the lower link is greater than zero when the distance between the upper and lower soles is at a minimum.

* * * * *